United States Patent
Neu et al.

(10) Patent No.: US 7,390,899 B2
(45) Date of Patent: Jun. 24, 2008

(54) PROCESS FOR THE SYNTHESIS OF HIGH PURITY 3,5-DIAMINO-6-(2,3-DICHLOROPHENYL)(1,2,4-TRIAZINE)

(75) Inventors: Jozsef Neu, Budapest (HU); Tibor Gizur, Budapest (HU); Jozsef Törley, Budapest (HU); Janos Csabai, Budapest (HU); Ferenc Vegh, Esztergom (HU); Peter Kalvin, Esztergom-Kertvaros (HU); Gabor Tarkanyi, Budaors (HU)

(73) Assignee: Richter Gedeon Vegyeszeti Gyar. RT., Budapest (HU)

( * ) Notice: Subject to any disclaimer, the term of this patent is extended or adjusted under 35 U.S.C. 154(b) by 0 days.

(21) Appl. No.: 10/528,379

(22) PCT Filed: Sep. 18, 2003

(86) PCT No.: PCT/HU03/00072

§ 371 (c)(1),
(2), (4) Date: Nov. 29, 2005

(87) PCT Pub. No.: WO2004/026845

PCT Pub. Date: Apr. 1, 2004

(65) Prior Publication Data

US 2006/0178511 A1    Aug. 10, 2006

(30) Foreign Application Priority Data

Sep. 20, 2002  (HU) .................................. 0203114

(51) Int. Cl.
C07D 253/075    (2006.01)
C07C 281/16     (2006.01)
(52) U.S. Cl. .................. 544/182; 558/388; 558/408
(58) Field of Classification Search ............... 544/182; 558/408, 388
See application file for complete search history.

(56) References Cited

U.S. PATENT DOCUMENTS 6,586,593 B1 * 7/2003 Guntoori et al. ............ 544/182

FOREIGN PATENT DOCUMENTS

| EP | 0 021 121 | 1/1981 |
|----|-----------|--------|
| EP | 0 247 892 | 12/1987 |
| EP | 0 963 980 | 12/1999 |
| WO | WO 96/20934 | 7/1996 |
| WO | WO 96/20935 | 7/1996 |
| WO | WO 01/49669 | 7/2001 |
| WO | WO 03/078407 | 9/2003 |

* cited by examiner

Primary Examiner—Venkataraman Balasubram
(74) Attorney, Agent, or Firm—Jonathan Myers; Andrew Wilford

(57) ABSTRACT

The present invention relates to a new process for the synthesis of high purity 3,5-diamino-6-(2,3-dichlorophenyl)-1,2,4-triazine of formula (I) using 2,3-dichlorobenzoyl cyanide and an aminoguanidine salt as starting materials. 2,3-dichlorobenzoyl cyanide is reacted with 1-2 mol equivalent of aminoguanidine salt in 3-6 mol equivalent of methanesulfonic acid, then the obtained adduct of formula (IV) is transformed without isolation into the product with magnesium oxide. In given case the obtained crude product can be recrystallized from a proper organic solvent

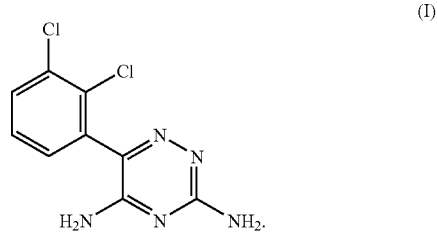

(I)

8 Claims, No Drawings

PROCESS FOR THE SYNTHESIS OF HIGH PURITY 3,5-DIAMINO-6-(2,3-DICHLOROPHENYL) (1,2,4-TRIAZINE)

CROSS REFERENCE TO RELATED APPLICATIONS

This application is the U.S. national phase of PCT application PCT/HU2003/000072 filed 18 Sep. 2003 with a claim to the priority of Hungarian patent application P0203114 itself filed 20 Sep. 2002.

FIELD OF THE INVENTION

The present invention relates to a process for the synthesis of high purity 3,5-diamino-6-(2,3-dichlorophenyl)-1,2,4-triazine of formula (I).

BACKGROUND OF THE INVENTION

It is well known, that 3,5-diamino-6-(2,3-dichlorophenyl)-1,2,4-triazine of the Formula (I)

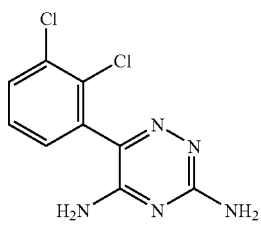

I also known as lamotrigine, is the active ingredient of several pharmaceutical compositions used for the treatment of different diseases of the central nervous system (e.g. epilepsy).

The synthesis of substituted 3,5-diamino-1,2,4-triazine derivatives is known from the literature. In the following publications the general synthesis of substituted derivatives is described—Agr. Res. Serif. 3 188 (1966) and J. Med. Chem. 859 (1972)—according to which benzoyl cyanide is reacted with aminoguanidine in acidic medium and the so obtained adduct is cyclized under basic conditions. According to the process described in the European Patent No. 21121—analogously to the method described above—2,3-dichlorobenzoyl cyanide is reacted with the hydrogencarbonate salt of aminoguanidine in dimethyl sulfoxide as solvent, in the presence of 8 N nitric acid for 7 days. The obtained adduct is cyclized with methanolic potassium-hydroxide solution to the final product in 15% yield—calculated on the starting material. Basically similar process is described in the European Patent No. 142306. The disadvantages of the above processes are the extremely aggressive reaction medium, the long reaction time as well as the very low yield.

The European Patent No. 247842 describes a process in which 8 M solution of sulfuric acid is used instead of 8 N nitric acid in the condensation reaction, and the reaction time is 48 h. The cyclization reaction is carried out in n-propanol at reflux temperature. The yield is 41%. The disadvantages of this process are the low yield and the aggressive reaction medium.

Basically similar process is described in the U.S. Pat. No. 6,111,101, in which the condensation is carried out in a mixture of diluted sulfuric acid and acetonitrile for 60 h, then the cyclization is carried out with 1% aqueous potassium hydroxide solution. The yield is 44%. The crude product is purified by recrystallization from methanol with the help of clarifier. The disadvantages of the process are the aggressive medium, the low yield and the very long reaction time.

The modification of the above process is described in the European Patent No. 963980, in which the cyclization reaction is carried out in n-propanol at reflux temperature. The yield is 60%. The product is purified by recrystallization from n-propano 1. The disadvantages of this process are also the long reaction time and the aggressive reaction medium.

According to the International Patent Application No. WO96120934 an intermediate, which is prepared with great difficulty, is converted into lamotrigine by cyclizing in a photo-chemical reactor in 80% yield. The disadvantage of the process is that it can not be applied on industrial scale.

The International Patent Application No. WO96120935 describes a six-step synthesis, which is difficult to carry out and hardly realizable on industrial scale, as well as the yield of the final product is very low. The disadvantages of the process are the complicated synthesis, the applied hazardous reagents and the low yield.

It is apparent from the above mentioned facts, that according to the known processes the lamotrigine and the intermediate adduct can only be synthesized in low yield using aggressive reagents and long reaction time. Our aim was to elaborate an industrially applicable process, in which simple industrial operations are used and high purity lamotrigine can be synthesized in good yield, economically, applying short reaction times, without using hazardous reagents.

OBJECT OF THE INVENTION

Therefore the object of the invention is a new process for the synthesis of high purity 3,5-diamino-6-(2,3-dichlorophenyl)-1,2,4-triazine of formula (I), using 2,3-dichlorobenzoyl cyanide as starting material and reacting it with the new dimesylate salt of aminoguanidine of formula (III) in the presence of methanesulfonic acid, then transforming the obtained adduct of formula (IV) without isolation into lamotrigine with magnesium oxide.

SUMMARY OF THE INVENTION

Surprisingly it was found, that on one hand the transformation of 2,3-dichlorobenzoyl cyanide of formula (II)

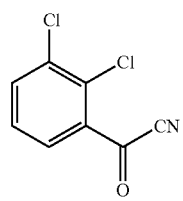

II into the adduct of formula (IV),

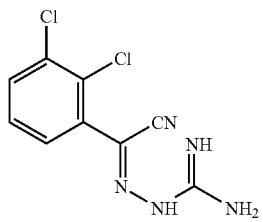

can be carried out in one hour using methanesulfonic acid as acidic medium and the yield of the adduct of formula (IV) is almost quantitative, therefore the use of large quantity of mineral acid is not necessary, on the other hand the reaction can be carried out in almost quantitative yield by applying the new dimesylate salt of aminoguanidine of formula (III)

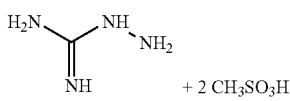

It was found furthermore, that the yield can be increased by using magnesium oxide as base in the cyclization reaction without lengthening the reaction time, and the formation of by-products can also be avoided. In the known procedures either strong base was applied, consequently the product always contained hydrolyzed by-product (e.g. the product synthesized according to the process of the European Patent No. 963980), or base was not used at all and therefore the cyclization reaction was not complete. The use of magnesium oxide eliminated all these difficulties.

During the elaboration of the recrystallization step it was found, that using acetone as solvent the product can be obtained in more than 99.9% purity and in 70% yield.

In a given case the so obtained crude lamotrigine is recrystallized from acetone using charcoal as clarifier.

The process of this invention has several advantages in contrast to the known procedures. The main advantage of the process of this invention is the production of high purity final product in almost quantitative yield. Further advantages of this process are the elimination of aggressive, hazardous reagents and the short reaction time compared to the known procedures. Considerable advantage of this process is furthermore that it does not require complicated industrial equipment of expensive structural material.

According to this invention the adduct formation reaction is carried out at 30-100° C., in 3-6 mol equivalent of methanesulfonic acid using 1-2 mol equivalent of aminoguanidine salt (both calculated on 2,3-dichlorobenzoyl cyanide starting material). The cyclization reaction is carried out without isolation of the adduct at 50-80° C. in the presence of 2-5 mol equivalent of magnesium oxide. The crude product can be recrystallized from a proper organic solvent using charcoal as clarifier.

According to this invention the adduct formation reaction can preferably be carried out at 70° C., in the presence of 4.2 mol equivalent of methanesulfonic acid, using 1.3 mol equivalent of dimesylate salt of amino guanidine and acetonitrile as cosolvent and the reaction time is one hour. The product is reacted with an aqueous suspension of 3.75 mol equivalent of magnesium oxide without isolation, preferably at 70° C. for 4 h. The hot magnesium salt is filtered off, and the filtrate is concentrated by distillation. The separated product is filtered off. The yield of the crude-lamotrigine is 90-95%, calculated on 2,3-dichlorobenzoyl cyanide.

In a given case the crude product is recrystallized from acetone using charcoal as clarifier to obtain high purity 3,5-diamino-6-(2,3-dichlorophenyl)-1,2,4-triazine, the total amount of impurities of which is less than 0.1%.

The invention is illustrated by the following non-limiting examples.

EXAMPLE 1

Aminoguanidine Dimesylate 13.61 g (0.1 mol) of aminoguanidine bicarbonate is suspended in 36 ml of methanol at 20-22° C. in a 250 ml round bottom flask, equipped with a magnetic stirrer, a thermometer, a reflux condenser and a dropping funnel. 21.14 g (0.22 mol) of methanesulfonic acid is added dropwise to the suspension over a period of 1.5 h, while the temperature of the reaction is allowed to rise to 40-45° C. After the addition the obtained solution is stirred at 65-70° C. for 15 min, then cooled to (−3)-(−5) ° C. and stirred at this temperature for 1 h. The precipitated crystals are filtered off and washed with 6.8 ml of methanol of (−3)-(−5) ° C.

The obtained crystalline material is dried in a vacuum oven at 45-50° C. and 6-10 kPa to give 23.46 g (88.10%) of the title compound as white crystals. Melting point: 147.5° C.

EXAMPLE 2

3,5-diamino-6-(2,3-diehlorophenyl)-1,2,4-triazine

A suspension of 24.0 g of methanesulfonic acid and 21.0 g (0.079 mol) of aminoguanidine dimesylate is warmed to 65-70° C. in a 500 ml round bottom flask, equipped with a stirrer, a thermometer and a dropping funnel. The mixture becomes homogenous after 15 min, then a solution of 12.0 g (0.06 mol) of 2,3-dichlorobenzoyl cyanide in 10 ml of acetonitrile is added dropwise. The obtained mixture is stirred at 65-70° C. for 1 h. A mixture of 9 g (0.223 mol) of magnesium oxide and 60 ml of water is stirred for 5 min and the obtained suspension is added to the reaction mixture over a period of 10 min.

The temperature of the reaction mixture is raised to 70° C. and kept at this temperature for 3 h. The hot reaction mixture is filtered, 90 ml of water is added to the filtrate and concentrated. 60 ml of water is added to the residue, the suspension is stirred at 0-5° C., then filtered off. The product is washed with water and dried at 60-70° C. to yield 14.3 g (93.1%) of the crude title compound. Melting point: 212-216° C.

EXAMPLE 3

Crystallization of 3,5-diamino-6-(2,3-diehlorophenyl)-1,2,4-triazine 10 g of 3,5-diamino-6-(2,3-dichlorophenyl)-1,2,4-triazine is dissolved in 400 ml of acetone at reflux temperature, then 0.5 g of charcoal is added and the mixture is refluxed for 5 min. The clarifier is filtered off and the filtrate is cooled to 0-5° C. The precipitated crystals are filtered off and dried at 90° C. in vacuum to yield 7.0 g (70%) of the product. Melting point: 215-219° C.

The invention claimed is:

1. A process for the synthesis of 3,5-diamino-6-(2,3-dichlorophenyl)-1,2,4-triazine of formula (I)

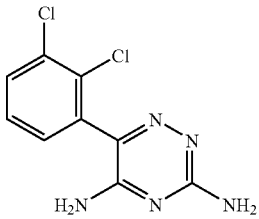

I which comprises the steps of:
(a) transforming 2,3-dichlorobenzoyl cyanide of formula (II)

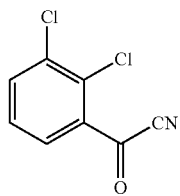

II with 1-2 mol equivalent of an aminoguanidine salt in 3-6 mol equivalent of methanesulfonic acid to obtain an adduct of the Formula (IV)

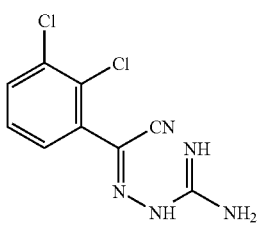

IV and,
(b) then transforming the obtained adduct of formula (IV) without isolation with magnesium oxide, to obtain the compound of the Formula (I).

2. The process defined in claim 1 further comprising the step of recrystallizing the obtained compound of the Formula (I) using an organic solvent.

3. The process defined in claim 1, wherein according to step (a) the aminoguanidine salt is the dimesylate salt of the formula (III)

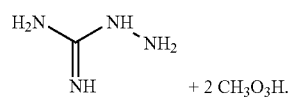

III

4. The process defined in claim 3, wherein according to step (a) 1.3 mol equivalent of aminoguanidine dimesylate of formula (III) are used per equivalent of the compound of the Formula (II).

5. The process defined in claim 1, wherein according to step (a) 4.2 mol equivalent of methanesulfonic acid are employed per equivalent of the compound of the Formula (II).

6. The process defined in claim 1, wherein according to step (b) the cyclization is carried out in the presence of 2-4 mol equivalent of magnesium oxide.

7. The process according to claim 6, wherein the cyclization is carried out by using 3.75 mol equivalent of magnesium oxide.

8. The process according to claim 2, wherein acetone is the organic solvent used for the recrystallization.

* * * * *